United States Patent
Diehr

(10) Patent No.: US 7,436,509 B2
(45) Date of Patent: Oct. 14, 2008

(54) MACHINE FOR INSPECTING GLASS CONTAINERS

(75) Inventor: Richard D. Diehr, Horseheads, NY (US)

(73) Assignee: Emhart Glass S.A., Cham (CH)

( * ) Notice: Subject to any disclaimer, the term of this patent is extended or adjusted under 35 U.S.C. 154(b) by 173 days.

(21) Appl. No.: 11/585,366

(22) Filed: Oct. 23, 2006

(65) Prior Publication Data
US 2008/0094617 A1    Apr. 24, 2008

(51) Int. Cl.
*G01N 21/00*   (2006.01)
(52) U.S. Cl. ................................... 356/239.4
(58) Field of Classification Search .............. 356/239.4
See application file for complete search history.

(56) References Cited

U.S. PATENT DOCUMENTS

| | | | | |
|---|---|---|---|---|
| 5,280,170 A | * | 1/1994 | Baldwin | 250/223 B |
| 6,031,221 A | * | 2/2000 | Furnas | 250/223 B |
| 7,057,718 B2 | * | 6/2006 | Kwirandt | 356/239.5 |
| 2003/0142299 A1 | * | 7/2003 | Kwirandt | 356/239.5 |
| 2005/0219523 A1 | * | 10/2005 | Onuma et al. | 356/239.5 |

* cited by examiner

*Primary Examiner*—Tarifur R. Chowdhury
*Assistant Examiner*—Isiaka O Akanbi
(74) *Attorney, Agent, or Firm*—Reinhart Boerner Van Deuren s.c.

(57) ABSTRACT

A machine for inspecting glass bottles for wire edges. A bottom light directs light vertically upwardly to image a Camera imaging the glass bottle from above. A beam splitter redirects light from a second light source which issues horizontal light, vertically downwardly towards the sealing surface. The bottle hole appears white, the sealing surface appears gray and the annular step appears black with a wire edge on the step appearing gray.

3 Claims, 2 Drawing Sheets

MACHINE FOR INSPECTING GLASS CONTAINERS

The present invention relates to machines which inspect the sealing surface of a glass container for a "wire edge".

BACKGROUND OF THE INVENTION

In the formation of a glass bottle, a gob of molten glass is first formed into a "parison" and then the parison is formed into a bottle. The parison may be formed in a pressing process where a plunger is advanced into a blank mold containing the gob to forcefully fill the space between the fully advanced plunger and the mold with molten glass. It is possible in this process to apply too much force which may result in a very slight opening of the molds with a very thin sliver of molten glass being pushed into this separation. This sliver extends upwardly from the inner edge of the bottle opening at the sealing surface of the bottle and is very undesirable.

OBJECT OF THE INVENTION

It is an object of the present invention to provide an apparatus for inspecting glass containers which can detect wire edges.

Other objects and advantages of the present portion of this invention will become apparent from the following accompanying drawings which illustrate, in accordance with the mandate of the patent statutes, a presently preferred embodiment incorporating the principles of the invention.

BRIEF DESCRIPTION OF THE DRAWINGS

The invention will become apparent from the following accompanying drawings which illustrate, in accordance with the mandate of the patent statutes, a presently preferred embodiment.

DETAILED DESCRIPTION OF THE PREFERRED EMBODIMENT

Figure 1:
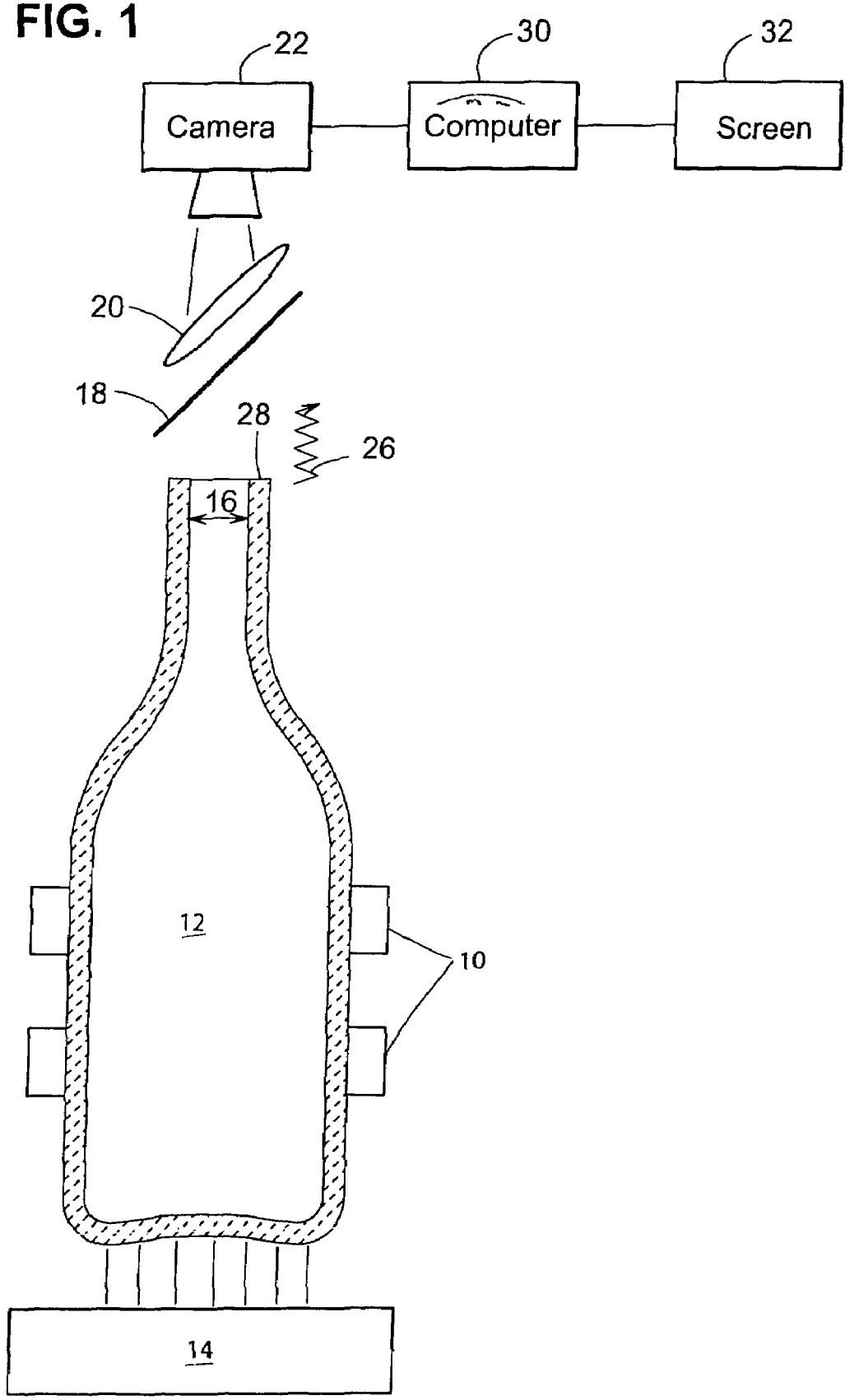
FIG. 1 is an elevational view of a glass inspection machine for inspecting for wire edges made in accordance with the teachings of the present invention.

The inspection machine has a belt type conveyor made up of opposed pairs of belts 10 which feed a glass bottle 12 to the disclosed inspection station. Beneath the glass bottle is a light source 14 which directs light axially through the bottle. The light passes through the bore 16 of the glass bottle, through a beam splitter 18, through a field lens 20 and into a camera 22, where the light will be imaged on the camera matrix. The image will be transferred to a computer 30 where it will be evaluated and a picture of the image will be displayed on a screen 32. A vertically oriented LED panel 26 directs light horizontally to the beam splitter 18 which reflects a portion of the light vertically, axially, downwardly at the top (sealing surface) 28 of the glass bottle.

Figure 2:
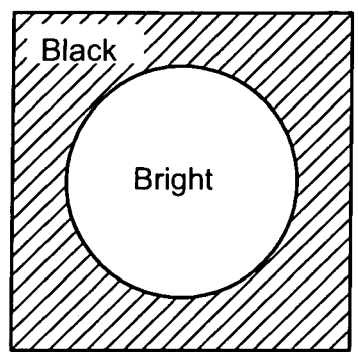
FIG. 2 is a view of the top surface of as bottle as imaged by the camera shown in FIG. 1.

FIG. 2 is an in image of the top of the glass bottle when the LED light source is turned off. The vertical hole in the finish of the glass bottle appears bright (white) while the rest of the image is black.

Figure 3:
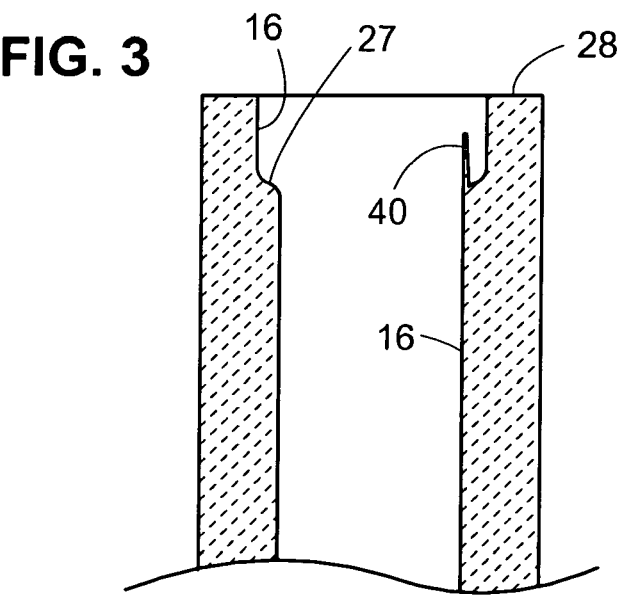
FIG. 3 is cross sectional view through the finish portion of the glass bottle

FIG. 3 shows the top of a bottle which has a flat sealing surface 24 and a very small inside step 26 which is slightly inclined (For purposes of clarity, this step is shown much larger than it would be). Projecting vertically upwardly is a "wire edge" 40 which can extend along a portion of the interior edge of the step. A wire edge is very undesirable since it may break off.

Figure 4:
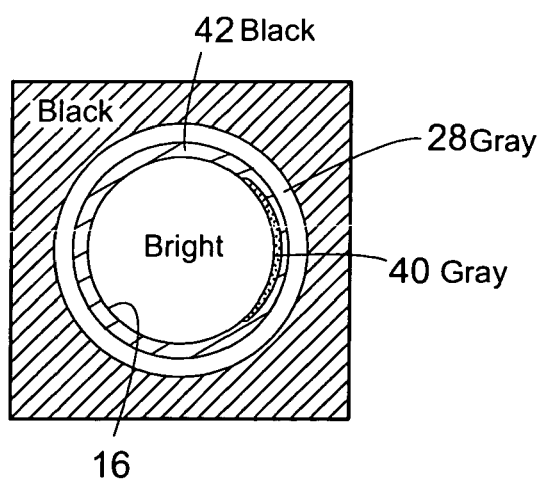
FIG. 4 is a view similar to FIG. 2 showing the presence of a wire edge.

FIG. 4 shows an image of the top of the glass bottle shown in FIG. 3 with the bottom 14 and LED 26 light sources "on". The hole in the finish continues to be bright or white. Enough light reflects upwardly from the sealing surface to make the sealing surface to appear gray. The annular Black area 42 between the Gray and Bright areas defines the annular step 26 with the wire edge 40 appearing Gray. The wire edge is highlighted and the lighting defines a well-defined annular black ring 42 in which a wire edge will be located.

The invention claimed is:

1. A machine for inspecting for the presence of a wire edge protruding upwardly from the inner edge of an annular step defined in the interior corner of the sealing surface hole of a glass bottle comprising means for vertically supporting the glass bottle at an inspection station, a first light source for directing light vertically upwardly through the bottom of the glass bottle, camera means, located vertically above the sealing surface, for imaging the sealing surface of the glass bottle, said camera means including a field lens located above the sealing surface, a beam splitter located between said field lens and the sealing surface, and a second light source directing light horizontally towards said beam splitter for redirecting the horizontally directed light vertically downwardly toward the sealing surface whereby the hole appears bright, the sealing surface appears gray, the annular step appears black and a wire edge appears gray.

2. A machine for inspecting for the presence of a wire edge according to claim 1, wherein said second light source is a panel of LED's.

3. A machine for inspecting for the presence of a wire edge according to claim 1, wherein said camera means includes a CCD camera.

* * * * *

(12) EX PARTE REEXAMINATION CERTIFICATE (7762nd)
United States Patent
Diehr

(10) Number: US 7,436,509 C1
(45) Certificate Issued: Sep. 21, 2010

(54) MACHINE FOR INSPECTING GLASS CONTAINERS

(75) Inventor: Richard D. Diehr, Horseheads, NY (US)

(73) Assignee: Emhart Glass S.A., Cham (CH)

Reexamination Request:
No. 90/010,351, Dec. 18, 2008

Reexamination Certificate for:
Patent No.: 7,436,509
Issued: Oct. 14, 2008
Appl. No.: 11/585,366
Filed: Oct. 23, 2006

(51) Int. Cl.
*G01N 21/00* (2006.01)

(52) U.S. Cl. .................................... 356/239.4
(58) Field of Classification Search .......... None
See application file for complete search history.

(56) References Cited

U.S. PATENT DOCUMENTS

| 4,435,641 | A | 3/1984 | Hajime |
| 4,682,023 | A | 7/1987 | Yoshida |
| 6,122,048 | A | 9/2000 | Cochran et al. |
| 2003/0112430 | A1 | 6/2003 | Lindner |

FOREIGN PATENT DOCUMENTS

| DE | 19920007 | 7/2000 |
| DE | 10065290 | 7/2002 |

*Primary Examiner*—Tuan H Nguyen

(57) ABSTRACT

A machine for inspecting glass bottles for wire edges. A bottom light directs light vertically upwardly to image a Camera imaging the glass bottle from above. A beam splitter redirects light from a second light source which issues horizontal light, vertically downwardly towards the sealing surface. The bottle hole appears white, the sealing surface appears gray and the annular step appears black with a wire edge on the step appearing gray.

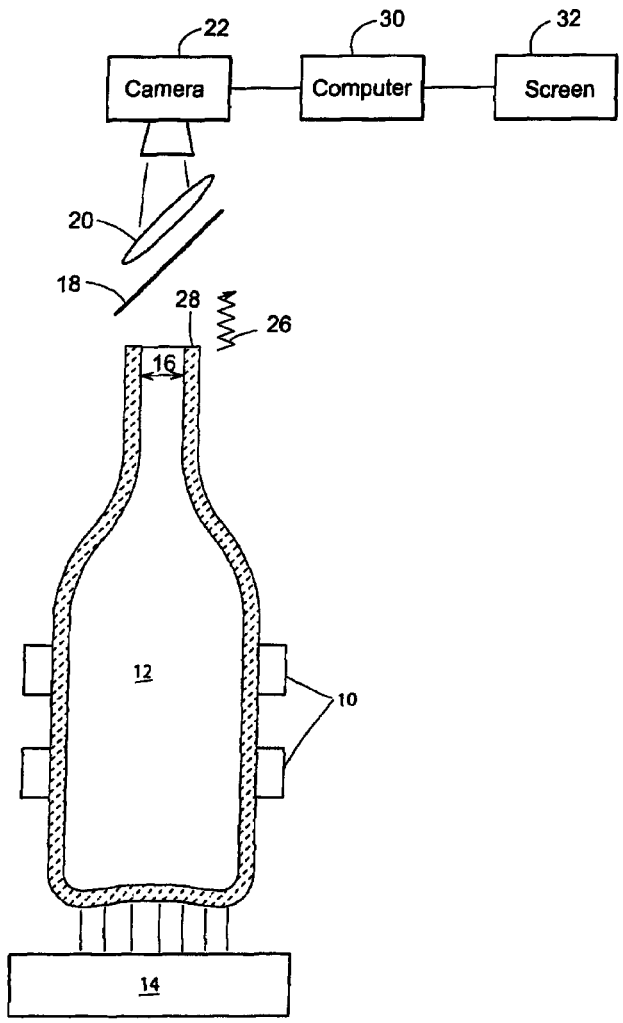

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claim 1 is determined to be patentable as amended.

Claims 2 and 3, dependent on an amended claim, are determined to be patentable.

1. A machine for inspecting for the presence of a wire edge protruding upwardly from the inner edge of an annular step defined in the interior corner of the sealing surface hole of a glass bottle comprising means for vertically supporting the glass bottle at an inspection station, a first light source for directing light vertically upwardly through the bottom of the glass bottle, camera means, located vertically above the sealing surface, for imaging the sealing surface of the glass bottle, said camera means including a field lens located above the sealing surface, a beam splitter located between said field lens and the sealing surface, and a second light source directing light horizontally towards said beam splitter for redirecting the horizontally directed light vertically downwardly toward the sealing surface whereby *in a single operation of the machine* the hole appears bright, the sealing surface appears gray, the annular step appears black and a wire edge appears gray.

* * * * *